United States Patent [19]

Cahill et al.

[11] Patent Number: 4,650,768
[45] Date of Patent: Mar. 17, 1987

[54] STABLE CHLORIDE TEST DEVICE

[75] Inventors: Sally E. Cahill, Union, Mich.; Melvin D. Smith, Wakarusa, Ind.

[73] Assignee: Miles Laboratories, Inc., Elkhart, Ind.

[21] Appl. No.: 697,511

[22] Filed: Feb. 1, 1985

[51] Int. Cl.[4] .................. G01N 21/82; G01N 33/52
[52] U.S. Cl. .................................. 436/125; 422/56; 422/58; 427/2
[58] Field of Search ................ 436/125; 422/56, 57, 422/58; 427/2

[56] References Cited

U.S. PATENT DOCUMENTS

| | | | |
|---|---|---|---|
| 3,092,464 | 6/1963 | Adams, Jr. et al. | 422/56 |
| 3,122,420 | 2/1964 | Rebar, Jr. et al. | 422/56 |
| 3,798,004 | 3/1974 | Zerachia et al. | 422/56 |
| 4,211,532 | 7/1980 | Tobari et al. | 436/125 X |
| 4,444,193 | 4/1984 | Fogt et al. | 436/125 X |

Primary Examiner—Arnold Turk

Attorney, Agent, or Firm—Mary G. Boguslaski

[57] ABSTRACT

A stable test device capable of manufacture by automated methods for the determination of chloride in an aqueous fluid sample. The test device operates by controlled diffusion of the aqueous sample into a porous matrix. The matrix is incorporated with sodium carrageenan and silver salts capable of dissolving in an aqueous fluid containing chloride, at least part of which silver salts is silver chromate. Devices prepared with the inclusion of sodium carrageenan provide a chloride test device with approximately double the shelf life under room temperature storage conditions of previous test devices prepared without sodium carrageenan. The stable test device provides useful information in less than about 2 minutes after the sample contacts the matrix. The chloride concentration of the sample is determined by comparing the pattern of silver chromate remaining after sample contact to an appropriate pattern chart.

9 Claims, 5 Drawing Figures

STABLE CHLORIDE TEST DEVICE

FIELD OF THE INVENTION

The invention relates in general to solid state test devices and in particular to a diffusion controlled chloride test device, a method for its preparation and its use.

UTILITY

The test device of the present invention provides a particularly stable device capable of monitoring the halide ion content, such as chloride, iodide and bromide ion, of an aqueous fluid sample which can be manufactured by automated methods. The determination of chloride ion concentration is useful industrially in such diverse processes as cement making and desalination plants, fish hatcheries and pickling brines and is useful medically.

Of the halides mentioned above, only chloride ion is present in significant amounts in body fluid samples. The presence of excess chloride in sweat has been used as a screening test for cystic fibrosis. In addition the excretion of chloride ion in the urine is tied to the excretion of cations such as sodium and potassium. Therefore chloride monitoring of urine content can be used as an indication of the concentration of sodium and/or potassium excreted.

INFORMATION DISCLOSURE

U.S. Pat. No. 4,046,514 discloses a test device wherein the carrier matrix comprises separate filaments formed into a cloth and at least one ingredient of the reactant system is incorporated with some of the filaments prior to their being formed into the cloth. In an example, VISCARIN ®, the registered trademark for sodium carrageenan, sold by Marine Colloids Inc., is used as a thickening agent. U.S. Pat. No. 4,038,485 discloses a test device example incorporating the same enzymatic test formulation including VISCARIN ® to which an inhibitor system was added to terminate the detectable response after a predetermined time.

Test devices which operate on a diffusion basis are known. U.S. Pat. No. 3,620,677 discloses an indicating device comprising a porous capillary material and an impervious covering material enclosing at least a major portion of the exterior surface of the capillary material. The device is constructed to provide directional guidance for movement of a fluid sample through the porous material. The porous wick material is impregnated with an indicator such as dichlorofluorescein. When it is also impregnated with a reactant such as silver nitrate, the device can measure the concentration of a salt solution, such as sodium chloride.

U.S. Pat. No. 3,798,004 discloses an improved dip-and-read type test device comprising a flat bibulous matrix incorporated with an indicator, the matrix being sandwiched between and attached to a pair of layers of liquid impervious members having exposed peripheral edges. Upon immersion into a solution, the bibulous material absorbs a sample and a color is developed if the suspected material is present in the solution. No specific examples of test systems or indicators are given.

U.S. Pat. No. 4,444,193 discloses a fluid absorbent quantitative test device comprising two concentric circular reaction areas of chemically treated absorbent paper. The sample is introduced through an inlet in the center of the first reaction circle. The preferred embodiment disclosed is a sweat test for chloride, intended as a screening test for cystic fibrosis. For such a chloride test the first reaction area is impregnated with a controlled amount of silver phosphate and the second reaction area is impregnated with silver chromate or silver dichromate. The sweat sample diffuses into the inlet of the first reaction area and the chloride present reacts with the silver phosphate. Any chloride over a predetermined amount reacted in the first reaction area diffuses into the second reaction area where its reaction with the silver chromate or dichromate provides a visible indication of the amount of sample chloride present in excess of the amount reacted in the first reaction zone.

Diffusion test devices, manufactured with automated equipment requiring a continuous feed stock roll of a porous carrier matrix incorporated with silver chromate or silver dichromate as an indicator, have been found to have poor stability when held under room temperature storage conditions (18 to 30 degrees centigrade). These devices therefore have a very short shelf life making them commercially impractical. The present invention solves this problem and provides a commercially feasible product with a shelf life double that of prior formulations manufactured by automated methods.

DESCRIPTION OF THE DRAWINGS

The drawing indicates the patterns which can be formed by a controlled diffusion test device for chloride, depending on where the opening, which allows contact of sample with the matrix, is placed.

FIG. 1 depicts the pattern formed by such a device after contact with a solution of about 0.1 percent sodium chloride.

FIG. 2 depicts the pattern formed after contact with a solution of about 0.4 percent sodium chloride.

FIG. 3 depicts the pattern formed after contact with a solution containing about 1.0 percent sodium chloride or greater.

Figure 1:
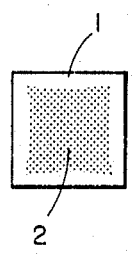
FIGS. 1 through 3 depict patterns formed by a preferred square test device covered by unconnected water impervious layers after uniform contact of all unconnected sides with different concentrations of sodium chloride solution.
Figure 2:
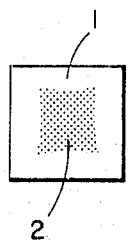
Figure 3:
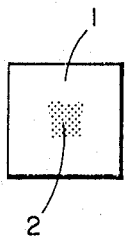
Figure 4:
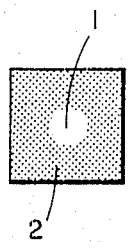
FIG. 4 depicts pattern formation if the sample opening is at the center of a square device.
Figure 5:
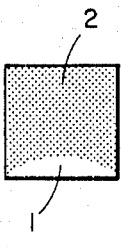
FIG. 5 depicts pattern formation if the sample is contacted only at one unconnected edge of the water impervious layers. Other edges can be fused or unconnected.

Area 1 in all figures indicates the white silver chloride precipitate area formed when the silver chromate or dichromate is dissolved by the chloride containing sample. Area 2 in all figures depicts the brown area of silver chromate/dichromate remaining after sample contact.

SUMMARY OF THE INVENTION

The invention provides a stable test device useful for the detection of chloride in an aqueous fluid sample, a method for its preparation and its use. A diffusion controlled stable test device comprising: (a) a porous carrier matrix said carrier matrix having at least two oppositely disposed surfaces, each surface having attached thereto a layer of water impermeable material, one of said layers being substantially transparent, said layered carrier matrix being open to accept sample in such a way as to allow controlled diffusion of the sample into the porous matrix; and (b) a test composition incorporated substantially uniformily therewith, said test composition comprising sodium carrageenan and silver salts capable of dissolving in an aqueous solution containing chloride ion, at least part of which chloride soluble silver salts is silver chromate. The addition of sodium carrageenan to the test composition provides improved storage stability. The projected shelf life of previous devices, manufactured with automated equipment, which were prepared without the addition of sodium carrageenan was only about 9 months, whereas the improved devices have a projected shelf life of at least 18 months or double those prepared with the previous formulation. The concentration of chloride in an aqueous fluid sample can be determined by contacting the test device with the sample for a time sufficient to wet the matrix and determining the pattern of the silver chromate remaining in the contacted test device. The pattern of silver chromate remaining is compared with standard patterns prepared for use with the device.

DETAILED DESCRIPTION OF THE INVENTION

A diffusion controlled test device for the determination of chloride in cement was previously marketed in small quantities under the name SALTEX® reagent strips by Ames Division, Miles Laboratories, Inc., Elkhart, Ind. During scale up work to provide a commercially feasible test for the determination of chloride in body fluids, product prepared by normal manufacturing procedures was found to have a very short shelf life, i.e., approximately 9 months. Reformulation to provide a product with commercially feasible shelf life was considered necessary. That work has resulted in the discovery that the inclusion of sodium carrageenan in the test composition provides such increased stability at elevated temperatures that a shelf life of 18 months to 2 years can be projected under room temperature storage conditions. Room temperature storage conditions are defined as storage between 18 and 30 degrees centigrade (°C). However, manufacturers normally test stability at the high temperature end of the range (28°-30° C.) to assure reasonable stability under the worst case conditions claimed. The carrageenan salt provides at least double the shelf life of formulations manufactured with automated equipment which were prepared without the carrageenan.

The operation of the test device of the present invention is based on diffusion and requires that uniform and reproducible patterns be developed in the device after contact with standardized aqueous chloride solutions. This is not the case for most other diagnostic solid state test devices. Therefore the stabilization of such a device could not be based on expected properties gleaned from manufacturing experience with other devices.

Sodium carrageenan is known to those skilled in the art of manufacturing solid state test devices as a thickener. While carrageenan is sometimes used to facilitate loading a carrier matrix with a test composition dissolved in an aqueous solution, its ability to stabilize silver chromate on a porous matrix was not predictable. It appears that the carrageenan stabilizes the silver salts in the test composition without impeding the diffusion of the aqueous fluid sample in such a way as to prolong the read time of the device beyond clinically useful limits. The improved formulation produced a diffusion controlled device which provided clinically useful information in less than about two minutes, preferably in about 30 to 60 seconds.

A. Test Composition

The test composition comprises sodium carrageenan and silver salts capable of dissolving in an aqueous fluid containing chloride, at least part of which chloride soluble silver salts is silver chromate. For the purposes of this application, silver chromate is considered equivalent to silver dichromate. The use of the term "silver chromate" can be interpreted as silver chromate, silver dichromate or mixtures thereof.

Sodium carrageenan is commercially available from Marine Colloids Division, FMC Corporation, Springfield, N.J., under the trademark VISCARIN®. Although many other materials including sugars such as dextrose and lactose, wetting agents, oxidants, alcohols and known stabilizers such as interpolymers of methylvinylether and maleic anhydride were used in attempts to increase the shelf life of the product, only sodium carrageenan worked to provide the desired characteristics in a test device which can be manufactured by automated methods requiring a continuous feed stock roll of porous carrier matrix. Other carrageenan salts which are soluble in water and do not interfere with the test system can be used. In order to provide a diffusion controlled, stable test device which could provide the desired information in a reasonably short time, less than about 2 minutes, no more than a total of 0.35 percent by weight of sodium carrageenan was added to the aqueous solutions used to incorporate the carrier matrix with the test composition. (Percent by weight is defined herein as gram per deciliter of solution.) The total weight percent of sodium carrageenan in the aqueous incorporating solutions can be 0.06 to 0.35 percent by weight; preferably 0.10 to 0.30 weight percent; and most preferably 0.10 to 0.25 weight percent. While it is preferred to add all the sodium carrageenan to the first incorporating solution, it can be added in a second incorporating solution or the total weight percent split between the incorporating solutions. Methods for the preparation of the test device are described more fully later in the specification.

The silver salts include any of those which are capable of dissolving in an aqueous fluid containing chloride. Suitable salts are silver phosphate, silver nitrate, silver sulfate, silver chromate and silver dichromate. At least part of the chloride soluble silver salts used should be silver chromate since the chromate salt is used as a visual marker. The dissolution of the silver chromate when contacted by an aqueous fluid sample containing chloride, provides an identifiable pattern in the diffusion controlled test device which can be related to the concentration of chloride in the sample. Silver salts which do not dissolve on contact with chloride containing aqueous solutions, would not be suitable in the test composition.

The concentration of silver ion is not critical, although the concentration of silver ion is related to the concentration range of chloride which the test device is able to determine. The chloride range will be approximately one-tenth to ten times the concentration of silver ion used. In urine, the clinical range of interest is from about 0.1 percent to 1 percent chloride.

B. Test Device

The test device is composed of a porous carrier matrix, substantially uniformily incorporated with the test composition, having at least two oppositely disposed surfaces, each surface attached to a layer of water impervious material. One of the layers of water impervious material should be substantially transparent.

Porous materials include any material which provide controlled diffusion of an aqueous sample. Suitable material include fibrous materials which contained interconnected void spaces such as cloth, paper, glass fibers and the like. Bibulous materials such as paper are preferred carrier materials.

The water impervious material can be any one of a number of plastic film materials such as polyethylene, polypropylene, polyvinyl polymers and copolymers as well as composite sheets such as polyethylene terephthalate (Mylar) as well as others disclosed in U.S. Pat. No. 3,620,677 incorporated herein by reference. One layer of the water impervious material should be transparent to allow visual determination of the test patterns formed after contact with a chloride containing aqueous fluid sample. A particularly preferred tape is "Scotchpar" film packaging tape available from 3M Company, St. Paul, Minn.

In order to obtain uniform, reproducible patterns after contact of the device with the sample, the placement of the sample opening in the water impervious material must be uniform. "Controlled diffusion" of the sample into the matrix refers to this limited, predetermined access of the sample with the matrix, to the rate of diffusion and to the limit of the amount of sample allowed to contact the matrix. The sample must enter the matrix at some predetermined point or points, diffuse through the matrix at a rate which allows dissolution of the chloride soluble salts, and for a reproducible pattern the sample should wet the entire pad. However, if an unlimited amount of sample is allowed to contact the matrix, all the silver chromate would dissolve leaving no discernible pattern for comparison.

C. Method of Preparation

A unitary solid state test strip or test device can be prepared by incorporation of the porous carrier matrix with drying between incorporation steps. Incorporation can be accomplished by any method such as dipping, spreading or spraying. Silver chromate can be incorporated by spraying the compound substantially uniformly into the porous matrix. Alternatively silver chromate can be formed in situ by precipitation. The precipitate is formed by impregnating the matrix twice, once with an aqueous solution containing a water soluble silver salt such as silver nitrate or silver phosphate and once with a solution containing a water soluble salt of chromate or dichromate such as potassium chromate. Mixtures of chromate or dichromate salts can also be used. The order of impregnation is not critical although it is preferred to impregnate the matrix with an aqueous solution of a water soluble silver salt such as silver nitrate or silver phosphate first, dry and then to impregnate the dried matrix with a water soluble chromate salt such as potassium chromate and dry. To form the particularly stable test device of the present invention, sodium carrageenan must be added to one of the impregnating solutions or split between impregnated solutions. A preferred method is to add the total amount of carrageenan to the first impregnating solution with the water soluble silver salt. The total concentration of carrageenan used to impregnate the matrix should be no more than 0.35 percent by weight. That amount can be added to either impregnating solution or split between the two solutions. This concentration provides a test device with a projected shelf life, under room temperature storage conditions, of at least 18 months which can still provide useful information in less than about 2 minutes.

Drying can be accomplished by any means which will not deleteriously affect the incorporated composition, usually by means of an heated oven. Each side of the doubly dried paper can be affixed to layers of water impervious material, one layer of which should be substantially transparent. The layered paper can be cut into any uniform geometric shape. Most convenient for automated manufacture is a square or rectangle. Cutting and affixing of the water impervious layers can be done in any convenient order. A preferred test device is formed when the layers of water impervious material are unconnected at all edges of the carrier matrix allowing uniform sample contact on all four sides. Alternatively, one layer can have a sample opening at some predetermined point and the layers can be sealed at the edges or the layers can be unconnected at one, two or three sides only.

The layered test device can be mounted on one end of a support member, for example a rigid or semirigid polystyrene film strip. Mounting of the paper on the strip can be accomplished through use of a double-faced adhesive tape, such as that commercially available from the 3M Company, St. Paul, Minn., under the trademark DOUBLE STICK ®. This adhesive itself can provide one water impervious layer. The support member provides a convenient handle which facilitates use of the test.

D. Method of Use

The test device can be used for the determination of chloride in an aqueous fluid sample by contacting the sample with the opening or openings in the water impervious layer to allow controlled diffusion of the sample into the porous matrix. Contact can be made by placing the device sample opening on the skin for collection of a sweat sample, by pipetting the sample onto the sample opening or by dipping a device into the sample fluid. If the opening is formed by leaving the layers of water impervious material unconnected at all edges, it is advantageous to dip the device into the sample to assure relatively instantaneous contact of sample at all points open to the matrix. When dipping, it is preferred that contact be sustained long enough to wet the entire pad in order to obtain reproducible patterns.

When an aqueous fluid containing chloride diffuses into the porous matrix, brown silver chromate is dissolved and a precipitate of silver chloride is formed according to the equation:

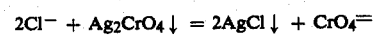

$$2Cl^- + Ag_2CrO_4 \downarrow\ = 2AgCl \downarrow\ + CrO_4^=$$

(brown)　　　(white)

The white color produced (or the pattern of brown silver chromate remaining) can be related to patterns formed by standard chloride solutions. Once enough sample has diffused into the matrix to wet the entire pad, the device is removed from sample contact. If a chloride containing sample is allowed to continue diffusing into the matrix, eventually all the silver chromate will dissolve and no pattern will be visible.

EXAMPLE

Stable test device for the detection of urinary chloride.

Whatman 3 MM filter paper was successively impregnated with the following solutions and dried at 100° C. after each impregnation:

| Solution 1: | |
| --- | --- |
| H$_2$O | 800 grams (g) |
| Sodium Carrageenan | 2.50 g |
| Silver Nitrate | 6.30 g |
| Ethanol | 162 g |
| Solution 2: | |
| H$_2$O | 800 g |
| Potassium Chromate | 1.83 g |
| Ethanol | 162 g |

The addition of ethanol to the impregnating solutions is not necessary but facilitates manufacturing. The resulting reagent paper was brown due to the formation of silver chromate in the paper with the second impregnation.

Transparent tape, available from 3M Company, St. Paul, Minn., was laminated onto one side of the reagent paper and the other side was laminated to a plastic handle with a water impervious adhesive. Strips which included a 0.5 cm square of laminated reagent paper were prepared. Edges of the water impervious layers were left unconnected.

When immersed in urine, the reagent pad absorbs urine through the surrounding cut edges and brown silver chromate is converted to off-white silver chloride by the chlorides in the urine. The greater the chloride content, the larger the white silver chloride area developed and the smaller the unreacted brown silver chromate area. The size of the brown area was compared to a pattern chart which provided three reference patterns for estimating chloride content up to at least 1.0 gram percent.

Prior test devices formulated without the addition of sodium carrageenan when stressed for twelve weeks at 40° C. showed an erroneous precipitate pattern indicating the presence of 0.7 gram percent sodium chloride when the aqueous sample contained only 0.4 gram percent sodium chloride. However, devices manufactured as indicated in this example show no shift in reading after similar stress tests and in fact show no shift after two weeks at 60° C. stress. It is therefore projected that the improved test device of the present invention will have a shelf life of at least 18 months, double the shelf life of previous devices.

Obviously, many modifications and variations of the invention as set forth may be made without departing from the spirit or scope of the invention.

What is claimed is:

1. A diffusion controlled stable test device useful for the determination of chloride in an aqueous fluid sample comprising:
   (a) a porous carrier matrix said carrier matrix having at least two oppositely disposed surfaces, each surface having attached thereto a layer of water impermeable material, one of said layers being substantially transparent, said layered carrier matrix being open to accept sample in such a way as to allow controlled diffusion of the sample into the porous matrix; and
   (b) a test composition incorporated substantially uniformly within said porous carrier matrix, said test composition comprising sodium carrageenan and silver salts capable of dissolving in an aqueous fluid containing chloride ion, at least part of which chloride soluble silver salts is silver chromate.

2. The stable test device of claim 1 in which the sample opening is formed by the water impervious layers being unconnected on at least one edge of the matrix.

3. The stable test device of claim 1 in which the sample opening is formed by the water impermeable layers being unconnected.

4. The stable test device of claim 1 in which one of the laminated water impermeable layers is affixed to a support member.

5. The stable test device of claim 1 in which the carrier matrix is paper.

6. The method for preparing a stable test device useful for the determination of chloride in an aqueous fluid sample, comprising the steps of:
   (a) incorporating a porous carrier matrix with a solution containing a water soluble silver salt and from 0.06 to 0.35 percent by weight sodium carrageenan;
   (b) drying the incorporated carrier;
   (c) incorporating the dried carrier with a solution containing a water soluble salt of chromate, dichromate or mixtures thereof;
   (d) drying the doubly incorporated carrier; and;
   (e) laminating each surface of the dried doubly incorporated matrix with layers of water impermeable material, one of the layers being substantially transparent, said layers being open at some point to permit contact of the aqueous fluid sample with the matrix.

7. The method of claim 6 in which the first incorporating solution contains from about 0.10 to about 0.30 percent by weight sodium carrageenan.

8. The method of claim 6 in which the first incorporating solution contains from about 0.12 to 0.25 percent by weight sodium carrageenan.

9. A process for determining chloride in an aqueous fluid sample, comprising the steps of:
   (a) contacting the test device of claim 1 with an aqueous fluid sample; and
   (b) determining the pattern of the silver chromate remaining in the contacted test device.

* * * * *